United States Patent [19]

Spietschka et al.

[11] Patent Number: 4,501,906

[45] Date of Patent: Feb. 26, 1985

[54] MONOALKALI METAL SALTS OF PERYLENE-3,4,9,10-TETRACARBOXYLIC ACID MONOANHYDRIDE AND PROCESS FOR THEIR MANUFACTURING

[75] Inventors: Ernst Spietschka, Idstein; Helmut Tröster, Königstein, both of Fed. Rep. of Germany

[73] Assignee: Hoechst Aktiengesellschaft, Frankfurt am Main, Fed. Rep. of Germany

[21] Appl. No.: 465,463

[22] Filed: Feb. 10, 1983

Related U.S. Application Data

[63] Continuation of Ser. No. 239,909, Mar. 3, 1981, abandoned.

[30] Foreign Application Priority Data

Mar. 5, 1980 [DE] Fed. Rep. of Germany ....... 3008420

[51] Int. Cl.³ .......................................... C07D 311/78

[52] U.S. Cl. ...................................... 549/232; 546/37
[58] Field of Search ......................................... 549/232

[56] References Cited

U.S. PATENT DOCUMENTS 3,628,976  12/1971  Stocker ............................... 549/232
3,872,103   3/1975  Fabian ................................ 549/232

*Primary Examiner*—Richard L. Raymond
*Attorney, Agent, or Firm*—Curtis, Morris & Safford

[57] ABSTRACT

Perylene-3,4,9,10-tetracarboxylic acid monoanhydride mono-sodium or mono-potassium salts are obtained from neutral salts of perylene-3,4,9,10-tetracarboxylic acid, if necessary in the presence of at least one molar equivalent of sodium or potassium ions, at 20° to 100° C. by adding three molar equivalents of a sufficiently strong acid. The products are dye precursors, especially for asymmetric N-substituted perylenetetracarboxylic acid diimide pigments.

8 Claims, No Drawings

MONOALKALI METAL SALTS OF PERYLENE-3,4,9,10-TETRACARBOXYLIC ACID MONOANHYDRIDE AND PROCESS FOR THEIR MANUFACTURING

This is a continuation of application Ser. No. 239,909 filed Mar. 3, 1981, now abandoned.

The present invention relates to monoalkali metal salts of perylene-3,4,9,10-tetracarboxylic acid monoanhydride of the formula 1

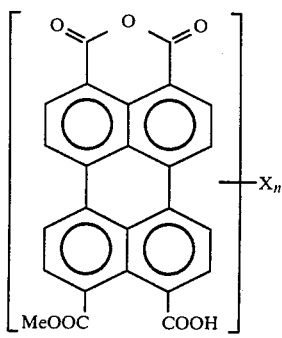

(1)

wherein

Me is a sodium or potassium ion,

X is chlorine or bromine and n is a number of from 0 to 4. Particularly preferred compounds of the formula 1 are those wherein Me is a potassium atom and those wherein n is zero.

The present invention further relates to a process for the preparation of the salts of formula 1, which comprises reacting salts of perylene-3,4,9,10-cetracarboxylic acid of the formula 2

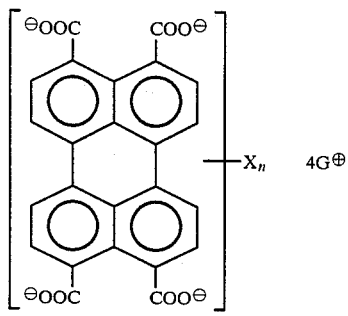

wherein

G+ is a cation and

X and n are defined as for formula 1 or preferably represent a tetraalkali metal or tetraammonium salt, in aqueous solution or suspension, if necessary in the presence of at least one molar equivalent of Me+, Me+ being defined as for formula 1, at a temperature of from 20° to 100° C., preferably 70° to 95° C., with three molar equivalents of an acid.

This process is suitably performed in the following manner: The perylenenetetracarboxylic acid or its anhydride is converted in water into the tetracarboxylate in usual manner at elevated temperature by adding the required quantity of a base. This reaction gives a suspension or solution, depending on the dilution degree. If the base used for the conversion into the tetracarboxylate is an amine, there has to be added at least the cation equivalent thereof, which is necessary for the monoalkali metal salt formation, in the form of a hydroxide or of a corresponding salt.

Excess base, if any, is neutralized with an acid, whereupon there are added 3 equivalents of acid per mol of perylenetetracarboxylic acid at 20° to 100° C. preferably at 70° to 95° C. When the acid addition is performed without heat supply, the reaction mixture is suitably heated thereafter to effect the conversion into the monoanhydride. Alternatively, the reaction product may be isolated without previous heating. During drying, it is converted into the monoanhydride.

The addition rate of acid is suitably adjusted such that the pH does not drop below 3, in order to reach a high purity of the product, the pH being preferably adjusted to a range of from 4 to 7.

The acid demand is given by the end point of the protonization, which is characterized by the fact that the pH jumps to 3.5–6.5.

The precipitated difficulty soluble monoalkali metal salt of perylene-3,4,9,10-tetracarboxylic acid monoanhydride may be isolated in usual manner by filtration.

Alternatively, it may be further reacted without intermediate isolation.

Suitable bases for dissolving the perylene-3,4,9,10-tetracarboxylic acid are in particular the hydroxides and carbonates of sodium and potassium. Suitable means are secondary and tertiary amines that are sufficiently basic for a conversion of perylenetetracarboxylic acid into its tetraammonium salt. Examples of amines are dimethyl amine, dibutyl amine, trimethyl amine, triethyl amine, diethanol amine or triethanol amine.

Suitable alkali metal ion donors are the hydroxides, chlorides, sulfates, nitrates or carbonates of sodium, in particular of potassium.

Suitable acids are strong mineral acids such as hydrochloric, sulfuric, nitric and phosphoric acid. Alternatively, there may be used acid salts such as sodium- or potassium hydrogen sulfate as well as organic acids such as acetic acid, propionic acid, trichloroacetic acid or toluenesulfonic acid.

The new compounds are valuable starting products for the manufacture of dyestuffs and pigments, in particular for the manufacture of asymmetric N-substituted perylenetetracarboxylic acid diimide pigments.

The present invention therefore also relates to the use of the new compounds in the manufacture of dyestuffs and pigments.

The following examples illustrate the invention. Percentages are by weight unless otherwise stated.

EXAMPLE 1

19.6 g of perylene-3,4,9,10-tetracarboxylic acid dianhydride and 8.3 g of 100% sodium hydroxide are dissolved in 2,500 ml of water at 80° C., whereupon the pH of the resultant solution is adjusted to 4.5 by adding dropwise 61 g of 10% hydrochloric acid at this temperature over a period of about 2 hours (single-cell-pH-meter). The suspension obtained is stirred for 2 hours at 80° C., during which period its pH rises only slightly to about 5.0. The reaction product is suction-filtered at 20°–25° C., washed chloride-free with water and dried.

Yield: 21.3 g.

Analysis: calc. Na: 5.3%. found Na: 3.5% ≙ 65.7% of the theory.

EXAMPLE 2

196 g of perylene-3,4,9,10-tetracarboxylic acid dianhydride are dissolved in 2,240 g of a 5% potassium hydroxide solution at 90° C. The resulting solution has a pH of about 10.5 (single-cell-pH-meter).

1,432 g of a 10% phosphoric acid are added dropwise over a period of 2-3 hours at 90° C., whereupon the pH has dropped to 5.0. The suspension is stirred for 1 hour at the same temperature, during which operation the pH remains practically unchanged. The precipitated bordeaux-colored potassium salt is suction-filtered at 20°-25° C., washed phosphate-free with water and dried at 110° C.

Yield: 220 g.

Analysis: calc. C: 64.3%; H: 2.0%; K: 8.7%. found C: 63.7%; H: 2.0%; K:8.6%.

The same good results are obtained when using instead of the 10% phosphoric acid the equivalent quantity (168 g) of a 85% phosphoric acid.

EXAMPLE 3

A mixture of 196 g of perylene-3,4,9,10-tetracarboxylic acid dianhydride, 2,000 ml of water and 132.9 g of 85% potassium hydroxide is heated to 90° C., during which operation the pH is 10-11. Thereafter the pH is adjusted to a practically constant value of 4.5-5.0 by adding dropwise 180 g of 31% hydrochloric acid at 90° C. over a period of about 2 hours. The suspension obtained is stirred for 1 hour and the precipitated potassium salt is suction-filtered while still hot and subsequently washed with hot water until free from chloride ions. Drying gives 219 g of a dark-red product, which is identical with the reaction product of Example 2.

EXAMPLE 4

19.6 g of perylene-3,4,9,10-tetracarboxylic acid dianhydride are added to a solution of 27.8 g of triethylamine in 500 ml of water and dissolved therein by heating to 80° C. 3.8 g of potassium chloride are added to the clear solution and subsequently there are added dropwise, at 80° C. over a period of 2-3 hours, 185 ml of 1 N-hydrochloric acid, a practically constant pH of 4-5 is established during this operation. A spot test using filter paper reveals a practically colorless solution. The product is stirred for about 2 hours at 80° C. and thereafter the precipitated dark-red microcrystalline potassium salt is isolated in usual manner. Yield: 21.9 g. Analysis: K: 7.6% ≙ 87.3% of the theory.

EXAMPLE 5

19.6 g of perylene-3,4,9,10-tetracarboxylic acid dianhydride are suspended in 2,500 ml of water and subsequently dissolved therein by adding 8.0 g of sodium hydroxide at 80° C. After addition of 3.8 g of potassium chloride the pH is adjusted to 7.5 with 1 N-hydrochloric acid and subsequently to a practically constant value of 4.5 by adding dropwise, over a period of about 2 hours, at 80° C., 150 ml of 1N-hydrochloric acid. After a stirring time of one hour the reaction product precipitated in the form of bordeaux-colored needles is isolated.

Yield: 21.5 g.

Analysis: K: 6.7%; Na 0.55% ≙ 87.3 of the theory (calculated on monoalkali metal salt).

EXAMPLE 6

38.6 g of 50% acetic acid are slowly added dropwise to 550 g of an aqueous solution containing 0.1 mol of the tetrapotassium salt of perylene-3,4,9,10-tetracarboxylic acid, at 90° C., until a practically constant pH of 6.2 is obtained. After a 1.5 hour's stirring time at 90° C. the product is suction-filtered in hot state and washed with hot water, which gives 43.8 g of monopotassium salt. The product corresponds to that obtained in Example 2.

EXAMPLE 7

547.5 g of 10% hydrochloric acid are added dropwise, at 20°-25° C., over a period of 30 minutes, to 2,600 ml of an aqueous solution containing 0.5 mol of the tetrapotassium salt of perylenetetracarboxylic acid. The batch is heated to 90° C. and maintained at this temperature for 30 minutes. The resulting reaction product corresponds to that obtained in Example 2.

Yield: 218 g.

EXAMPLE 8

109 g of 10% hydrochloric acid are added dropwise, at 20°-25° C., within about 3 hours, to 606.3 g of a 0.1 molar solution of the tetrapotassium salt of perylenetetracarboxylic acid. The pH of the solution is 6-7. Subsequently the pH is adjusted to 5.0-5.5 by adding 1 g of 10% hydrochloric acid. After some hours the reaction product is isolated in usual manner and dried.

Yield: 42.5 g.

Analysis: K: 7.8% ≙ 89.6% of the theory.

EXAMPLE 9

23.6 g of bromoperylenetetracarboxylic acid dianhydride (bromine content 14.4% ≙ 0.82 Br atoms) are dissolved in 500 ml of water by adding 13.2 g of 88% potassium hydroxide at 80° C. The pH is subsequently adjusted to 4-5 by adding dropwise 56 g of 10% hydrochloric acid at 80° C. The potassium salt obtained is isolated after 1 hour.

Yield: 25.7 g.

Analysis: K: 6.6%; Br: 12.8%.

The bromoperylenetetracarboxylic acid dianhydride was prepared according to Example 1 of German Offenlegungsschrift No. 2,519,790 using, however, instead of chlorine, the equivalent quantity of bromine.

EXAMPLE 10

26.5 g of tetrachloroperylenetetracarboxylic acid dianhydride (chlorine content 27.2%), prepared according to Example 3 of German Offenlegungsschrift No. 2,519,790, are dissolved at 80° C. in 500 ml water and 13.2 g of 85% potassium hydroxide. The pH is subsequently adjusted to 3-4 by adding dropwise 57 g of 10% hydrochloric acid, at the above temperature and the precipitated reaction product is isolated from the hot solution after stirring for 1 hour. 25.7 g of the corresponding monoanhydride monopotassium salt are obtained.

Analysis: Cl: 24.5%. K: 6.3%.

We claim:

1. A compound of the formula

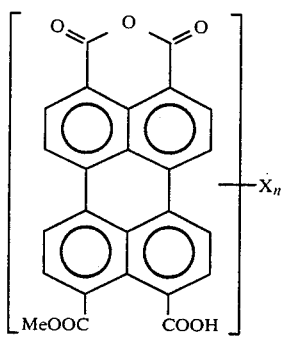

wherein Me is potassium, X is chlorine or bromine and n is a nunmber of from zero to 4.

2. A compound as claimed in claim 1, wherein n is zero.

3. A process for preparing a compound as defined in claim 1, which comprises reacting a salt of the formula

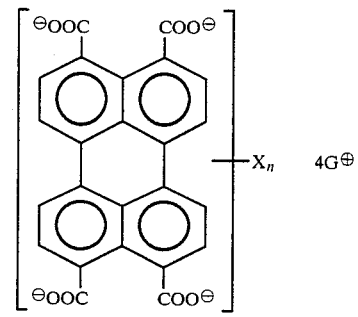

wherein X and n are defined as in claim 1 and G+ is a cation at a temperature of 20° to 100° C. with three molar equivalents of an acid sufficiently strong to set free the acid form of three of the carboxylic acid groups, said reaction being carried out in the presence of at least one molar equivalent of potassium if no G+ is potassium.

4. A process as claimed in claim 3, wherein the temperature is from 70° to 95° C.

5. A process as claimed in claim 3, wherein the reaction is performed in a pH range below 3.

6. A process as claimed in claim 3, wherein the reaction is performed in a pH-range of 4 to 7.

7. A process as claimed in claim 3, wherein the acid is hydrochloric acid, sulfuric acid, nitric acid or phosphoric acid.

8. A process as claimed in claim 3, wherein G+ is a sodium or potassium cation or an ammonium cation.

* * * * *